US012514967B2

(12) United States Patent
Wenthold

(10) Patent No.: US 12,514,967 B2
(45) Date of Patent: Jan. 6, 2026

(54) PLASMA DETOXIFICATION METHODS AND SYSTEMS

(71) Applicant: MARKER HOLDINGS AG, Zug (CH)

(72) Inventor: RAndy Wenthold, Menahga, MN (US)

(73) Assignee: MARKER HOLDINGS AG (CH)

( * ) Notice: Subject to any disclaimer, the term of this patent is extended or adjusted under 35 U.S.C. 154(b) by 188 days.

(21) Appl. No.: 16/741,429

(22) Filed: Jan. 13, 2020

(65) Prior Publication Data

US 2020/0222615 A1 Jul. 16, 2020

Related U.S. Application Data

(60) Provisional application No. 62/791,617, filed on Jan. 11, 2019.

(51) Int. Cl.

| | |
|---|---|
| ***A61M 1/34*** | (2006.01) |
| ***A61M 1/02*** | (2006.01) |
| ***A61M 1/36*** | (2006.01) |

(52) U.S. Cl.

CPC ........ *A61M 1/3472* (2013.01); *A61M 1/0231* (2014.02); *A61M 1/029* (2013.01); *A61M 1/3673* (2014.02); *A61M 2202/0415* (2013.01)

(58) Field of Classification Search

CPC .. A61M 1/0231; A61M 1/029; A61M 1/3468; A61M 1/3472; A61M 1/3486;

(Continued)

(56) References Cited

U.S. PATENT DOCUMENTS 4,228,015 A 10/1980 De Vries et al.
4,243,532 A 1/1981 Tsuda et al.

(Continued)

FOREIGN PATENT DOCUMENTS

CN 105056325 A 11/2015
CN 105916532 A 8/2016

(Continued)

OTHER PUBLICATIONS

National Intellectual Property Center, Georgia (GE), Inquiry and Search Report issued in the counterpart Georgian Application No. AP 2020-15715 on Nov. 22, 2022.

(Continued)

*Primary Examiner* — Dirk R Bass

(74) *Attorney, Agent, or Firm* — FisherBroyles, LLP; James W. Hill; Andrew K. Gonsalves

(57) ABSTRACT

Disclosed are methods, systems, and devices for removing cytokines and other substances from blood of a subject in a closed fluid circuit. The methods, systems, and devices involve: (i) passing venous blood from the subject through a plasma separator, thereby separating the blood into blood cells and plasma; (ii) passing the plasma received from the plasma separator through an adsorption chamber located in the circuit to form processed plasma, where materials in the adsorption chamber adsorb cytokines in the plasma to form the processed plasma, and where the materials include, by weight, 50-70% activated carbon and 30-50% non-ionic resin; (iii) combining the processed plasma, received directly from the adsorption chamber, with the blood cells in a combining chamber to form processed blood, without exchanging any of the plasma for another fluid; and (iv) transfusing the processed blood from the circuit directly into the subject, where no fluid besides the subject's blood is added to the circuit before the transfusing of the processed blood into the subject is completed.

19 Claims, 2 Drawing Sheets

(58) Field of Classification Search
CPC .............. A61M 1/3496; A61M 1/3673; A61M 2202/0415
See application file for complete search history.

(56) References Cited

U.S. PATENT DOCUMENTS

| | | | | |
|---|---|---|---|---|
| 4,388,163 | A | | 6/1983 | Richter et al. |
| 4,518,497 | A | | 5/1985 | Tsuda et al. |
| 5,543,062 | A | | 8/1996 | Nishimura |
| 5,700,372 | A | | 12/1997 | Takesawa et al. |
| 5,744,042 | A | | 4/1998 | Stange et al. |
| 5,858,238 | A | | 1/1999 | McRea et al. |
| 5,971,158 | A | * | 10/1999 | Yager ........................ B03B 5/00 209/208 |
| 6,113,785 | A | | 9/2000 | Miura et al. |
| 6,262,172 | B1 | | 7/2001 | Yu et al. |
| 6,284,141 | B1 | | 9/2001 | Shaldon et al. |
| 6,287,516 | B1 | | 9/2001 | Matson et al. |
| 6,319,662 | B1 | | 11/2001 | Foley et al. |
| 6,632,359 | B1 | | 10/2003 | Uezumi et al. |
| 6,733,471 | B1 | | 5/2004 | Ericson et al. |
| 6,878,127 | B2 | | 4/2005 | Brady et al. |
| 7,087,168 | B2 | | 8/2006 | Oishi et al. |
| 7,153,473 | B2 | | 12/2006 | Ericson et al. |
| 7,264,607 | B2 | | 9/2007 | Caleffi |
| 7,312,023 | B2 | | 12/2007 | Brady et al. |
| 7,441,666 | B2 | | 10/2008 | Kim et al. |
| 7,556,768 | B2 | | 7/2009 | Brady et al. |
| 7,563,376 | B2 | | 7/2009 | Oishi |
| 7,591,948 | B2 | | 9/2009 | Muller et al. |
| 7,597,806 | B2 | | 10/2009 | Uchi et al. |
| 7,618,542 | B2 | | 11/2009 | Okazaki |
| 7,621,884 | B2 | | 11/2009 | Goehl et al. |
| 7,695,958 | B2 | | 4/2010 | Funatsu et al. |
| 7,748,275 | B2 | | 7/2010 | Kouda et al. |
| 7,846,650 | B2 | | 12/2010 | Brady et al. |
| 7,862,660 | B2 | | 1/2011 | Murawski et al. |
| 8,038,638 | B2 | | 10/2011 | Roberts et al. |
| 8,202,241 | B2 | | 6/2012 | Karakama et al. |
| 8,329,388 | B2 | | 12/2012 | Brady et al. |
| 8,334,094 | B2 | | 12/2012 | Brady et al. |
| 8,349,550 | B2 | | 1/2013 | Brady et al. |
| 8,408,040 | B2 | | 4/2013 | Kouda et al. |
| 8,602,221 | B2 | | 12/2013 | Mizomoto et al. |
| 8,691,146 | B2 | | 4/2014 | Sato et al. |
| 8,708,945 | B2 | | 4/2014 | Kusunoki et al. |
| 8,758,286 | B2 | | 6/2014 | Ward et al. |
| 8,771,215 | B2 | | 7/2014 | Tonelli et al. |
| 9,259,710 | B2 | | 2/2016 | Rempfer et al. |
| 9,408,962 | B2 | | 8/2016 | Ward et al. |
| 9,526,735 | B2 | | 12/2016 | Kusunoki et al. |
| 9,550,019 | B2 | | 1/2017 | Buck et al. |
| 9,616,393 | B2 | | 4/2017 | Hidaka et al. |
| 9,707,328 | B2 | | 7/2017 | Pudil et al. |
| 9,707,330 | B2 | | 7/2017 | Kelly et al. |
| 9,713,666 | B2 | | 7/2017 | Pudil et al. |
| 9,821,105 | B2 | | 11/2017 | Yeh et al. |
| 9,844,621 | B2 | | 12/2017 | Rempfer et al. |
| 9,849,427 | B2 | | 12/2017 | Kuroda et al. |
| 9,956,334 | B2 | | 5/2018 | Ichi et al. |
| 9,974,895 | B2 | | 5/2018 | Storr et al. |
| 10,022,481 | B2 | | 7/2018 | Hornung et al. |
| 10,029,216 | B2 | | 7/2018 | Hori et al. |
| 10,086,123 | B2 | | 10/2018 | Welzel et al. |
| 10,086,126 | B2 | | 10/2018 | Ward et al. |
| 10,098,993 | B2 | | 10/2018 | Meyer et al. |
| 10,188,991 | B2 | | 1/2019 | Menda et al. |
| 10,195,327 | B2 | | 2/2019 | Meyer et al. |
| 10,201,648 | B2 | | 2/2019 | Lombardo et al. |
| 10,232,320 | B2 | | 3/2019 | Hata et al. |
| 10,238,785 | B2 | | 3/2019 | Storr et al. |
| 10,265,453 | B2 | | 4/2019 | Flieg et al. |
| 10,342,912 | B2 | | 7/2019 | Yeh et al. |
| 2001/0051106 | A1 | | 12/2001 | Matson et al. |
| 2003/0029785 | A1 | * | 2/2003 | Dannenmaier ...... B01D 63/022 210/263 |
| 2004/0034317 | A1 | * | 2/2004 | Gorsuch ............. A61M 1/1682 604/5.02 |
| 2004/0228829 | A1 | | 11/2004 | Roberts et al. |
| 2005/0281809 | A1 | | 12/2005 | Roberts et al. |
| 2007/0181499 | A1 | * | 8/2007 | Roberts ............... A61M 1/3486 210/663 |
| 2012/0267290 | A1 | | 10/2012 | Hochrein et al. |
| 2014/0358060 | A1 | * | 12/2014 | Laster ..................... A61M 1/34 604/6.09 |
| 2017/0173231 | A1 | | 6/2017 | Kiriyama et al. |

FOREIGN PATENT DOCUMENTS

| | | | |
|---|---|---|---|
| CN | 108310503 | A | 7/2018 |
| EP | 0787500 | B1 | 12/1999 |
| JP | S5717658 | A | 1/1982 |
| JP | H06237997 | A | 8/1994 |
| JP | H0833706 | A | 2/1996 |
| JP | 2005110832 | A | 4/2005 |
| JP | 2010069306 | A | 4/2010 |
| JP | 2012501701 | A | 1/2012 |
| KR | 20130131437 | A | 12/2013 |
| WO | 2005082504 | A2 | 9/2005 |
| WO | 2006002151 | A1 | 1/2006 |
| WO | 2017205720 | A1 | 11/2017 |

OTHER PUBLICATIONS

Taiwan Patent Application No. 10900975 Search Report dated Sep. 13, 2023.

Japanese Patent Application No. 2021-539946 Office Action dated Nov. 10, 2023. English Translation.

Korean Patent Application No. 10-2021-7025009 Office Action dated Dec. 12, 2024 with English Translation.

European Patent Application No. 20702378.9 Examination Report dated Oct. 29, 2024.

* cited by examiner

PLASMA DETOXIFICATION METHODS AND SYSTEMS

CROSS-REFERENCE TO RELATED APPLICATIONS

This application claims priority benefit of U.S. Provisional Patent Application Ser. No. 62/791,617, filed Jan. 11, 2019, the disclosure of which is hereby incorporated by reference herein in its entirety.

TECHNICAL FIELD

The present disclosure provides, inter alia, methods, systems, and devices for plasma detoxification using a closed fluid circuit.

BACKGROUND

Sepsis is the primary cause of death in the intensive care unit and more than 35% of patients are admitted with sepsis or develop it during their intensive care unit stay. Hospital mortality rates are 27%, reaching 54% in the case of septic shock. Extracorporeal blood purification therapies have been proposed to improve outcomes for patients with sepsis. These therapies are based on the principle that removal of inflammatory mediators or bacterial toxins (or both) from the blood will favorably modulate the host inflammatory response. Recently, significant technological progress has greatly broadened the spectrum of techniques available for blood purification. Promising results have been reported with high-volume hemofiltration (HVHF), cascade hemofiltration, hemoadsorption, plasmapheresis, coupled plasma filtration adsorption (CPFA), high-adsorption hemofiltration, and high-cutoff (HCO) hemodialysis/hemofiltration. However, these techniques have not entered into mainstream clinical practice around the world.

Many doctors view sepsis as a three-stage syndrome, starting with sepsis and progressing through severe sepsis to septic shock. The goal is to treat sepsis during its early stage, before it becomes more dangerous.

Plasma detoxification systems with extracorporeal circuits having plasma filter devices incorporated therein are known in the art. See, e.g., U.S. Pat. No. 8,038,638 (Hemolife Medical) (hereinafter "the '638 patent") and European Patent No. EP 0787500 A1 (Bellco) (hereinafter "the '500 patent"). These plasma detoxification systems are described as effective to treat sepsis, renal failure, and liver failure. There are several deficiencies with these systems. For example, an acute renal failure pump that must possess a plasma adsorption mode is required in combination with the plasma separation filter device and the adsorptive toxin removal device. These systems also require complex tubing connections to be effective. Furthermore, these systems must be used with anticoagulation to function. Sodium heparin, which is the anticoagulant used in these systems, is expensive and difficult to dose during the therapy, and can be an issue for patients subject to bleeding.

No one extracorporeal system known in the art has been successful in the market place due to the esoteric tubing requirements and sodium heparin anticoagulation requirements used to manage the treatment. Previous systems also have made sepsis treatment more difficult to manage by attempting to combine fluid removal via a hemofilter device. Anticoagulation control of the patient's blood without excess plasma fluid removal is itself difficult. Thus, adding excess plasma fluid removal while simultaneously controlling the patient's blood clotting via sodium heparin anticoagulation is a difficult clinical practice and a reason why the current systems known in the art have not been successful in the market. Intensive Care Unit (ICU) treatment associated with all existing extracorporeal devices introduced for treatment is another reason why previous systems have not been successful in the market. Therefore, there remains a need for a safe and effective extracorporeal system for plasma detoxification.

The present invention is directed to overcoming these and other deficiencies in the art.

SUMMARY

The present disclosure provides, inter alia, methods, systems, and devices for plasma detoxification using a closed fluid circuit. As described herein, the methods, systems, and devices of the present disclosure provide an extracorporeal system that can be used to safely remove toxins from plasma in patients suffering from many forms of sepsis, liver failure, acute respiratory distress, viral infections, poisoning, inflammation, and many other diseases and conditions treatable by plasma detoxification. In accordance with the present disclosure, the methods, systems, and devices provided herein are improvements over the existing art because they can use standard venous blood access with a centrifugal apheresis pump or similar device, thereby enabling therapeutic treatments to be administered as an out-patient type service instead of being limited to an ICU treatment.

In one aspect, the present disclosure provides a system for removing cytokines and other substances from blood of a subject in a closed fluid circuit. This system includes components effective to perform the following method steps: (i) passing venous blood from the subject through a plasma separator, thereby separating the blood into blood cells and plasma; (ii) passing the plasma received from the plasma separator through an adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin; (iii) combining the processed plasma, received directly from the adsorption chamber, with the blood cells in a combining chamber to form processed blood, without exchanging any of the plasma for another fluid; and (iv) transfusing the processed blood from the circuit directly into the subject, wherein no fluid besides the subject's blood is added to the circuit before the transfusing of the processed blood into the subject is completed.

In another aspect, the present disclosure provides a system for use in the therapeutic treatment of a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment, wherein said system comprises a plasma separator, an adsorption chamber, and a combining chamber, and wherein said system is used for said therapeutic treatment of the disease or condition by removing cytokines and other substances from blood of a subject in a closed fluid circuit, said system being effective to perform the following method steps: (i) passing venous blood from the subject through the plasma separator, thereby separating the blood into blood cells and plasma; (ii) passing the plasma received from the plasma separator through the adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin; (iii) combining the processed plasma, received directly from the adsorption chamber, with the blood cells in the combining chamber to form processed blood, without exchanging any of the plasma for another fluid; and (iv) transfusing the processed blood from the circuit directly into the subject, wherein no fluid besides the subject's blood is added to the circuit before the transfusing of the processed blood into the subject is completed.

In another aspect, the present disclosure provides for the use of an adsorption chamber for the manufacture of a system according to the present disclosure for the therapeutic treatment of a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment.

In another aspect, the present disclosure provides a method of removing cytokines and other substances from blood of a subject in a closed fluid circuit. This method involves the steps of: (i) passing venous blood from the subject through a plasma separator, thereby separating the blood into blood cells and plasma; (ii) passing the plasma received from the plasma separator through an adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin; (iii) combining the processed plasma, received directly from the adsorption chamber, with the blood cells in a combining chamber to form processed blood, without exchanging any of the plasma for another fluid; and (iv) transfusing the processed blood from the circuit directly into the subject, wherein no fluid besides the subject's blood is added to the circuit before the transfusing of the processed blood into the subject is completed.

In another aspect, the present disclosure provides a method for therapeutic treatment of a subject. This method involves performing the method of removing cytokines and other substances from blood of a subject in a closed fluid circuit as described herein, thereby providing therapeutic treatment to the subject.

In certain embodiments, the methods, systems, and devices of the present disclosure involves the use of an adsorptive toxin removal device with a centrifugal apheresis pump to effectively detoxify plasma from patients suffering from various diseases. As described in more detail herein, the methods, systems, and devices of the present disclosure are advantageous over the existing art in that they reduce the number and complexity of devices, tubing, and components required for treatment. Furthermore, the methods, systems, and devices of the present disclosure can use anticoagulant citrate dextrose solution ACD-A, rather than being limited to using sodium heparin for the anticoagulant. The methods, systems, and devices of the present disclosure are also advantageous in that they incorporate effective device design for easy manufacture, and enable an assembly method to manufacture small scale devices for valuable scale-up laboratory studies or for use with small to medium sized patient's, including children.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
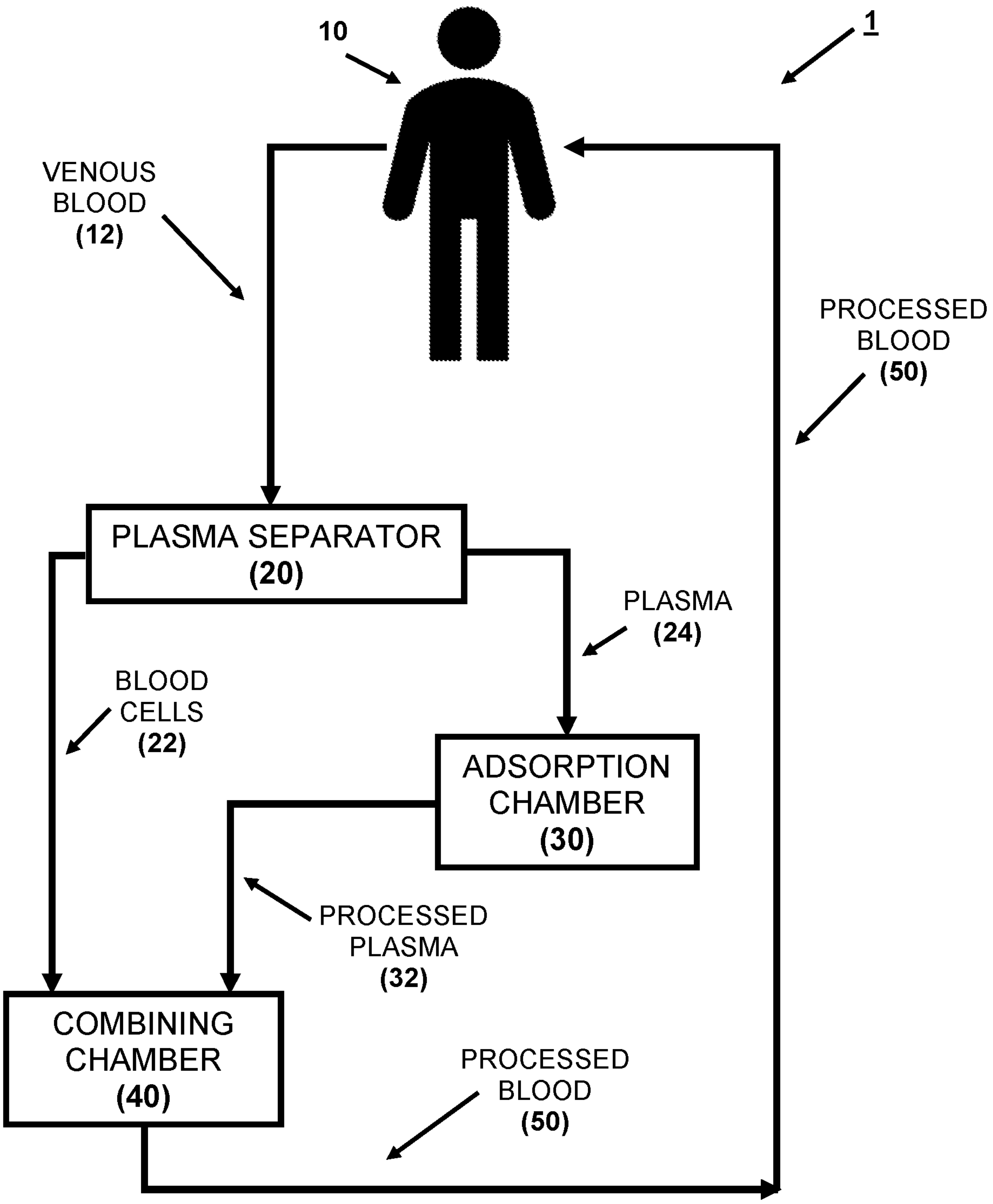
FIG. 1 is a schematic of an exemplary embodiment of a system for removing cytokines and other substances from blood of a subject in a closed fluid circuit, as provided in the present disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The instant disclosure is directed to, inter alia, methods, systems, and devices for plasma detoxification using a closed fluid circuit. As described herein, the methods, systems, and devices of the present disclosure provide an extracorporeal system that can be used to safely remove cytokines and other toxins and unwanted substances from the plasma of patients suffering from various diseases and conditions including, as described in more detail herein.

As used herein, the term "cytokines" refers to a broad category of small proteins (~5-20 kDa) that are important in cell signaling. Cytokines may include, without limitation, chemokines, interferons, interleukins, lymphokines, and tumor necrosis factors. Cytokines can be produced by a broad range of cells, including, for example, immune cells like macrophages, B lymphocytes, T lymphocytes and mast cells, as well as endothelial cells, fibroblasts, and various stromal cells.

As used herein, the terms "toxins" and "substances" (also referred to as "unwanted substances") refer to any organic or inorganic compound that, when present in a subject's blood above a tolerable threshold, causes an adverse effect on the subject. Representative examples of toxins in accordance with the present disclosure include, without cytokines including interleukins (including but not limited to, IL-3), interferons, tumor necrosis factors alpha or gamma, soluble proteins, bilirubin, creatinine, amino acids, nucleic adds, bacterial toxins including; endotoxins, exotoxins, lipopolysacccharides, cellular enzymes, bacterial cell wall components and pharmaceuticals such as acetaminophen.

In accordance with the present disclosure, the methods, systems, and devices provided herein enable standard venous blood access with a centrifugal apheresis pump or similar device, thereby enabling therapeutic treatments to be administered in an out-patient type manner rather than such therapeutic treatments being limited to an ICU setting.

In one aspect, the present disclosure is directed to a system for removing cytokines and other substances from blood of a subject in a closed fluid circuit. As described in more detail herein, the system is an extracorporeal plasma detoxification system that includes components and devices that are effective to carry out the methods of the present disclosure. At a minimum the system of the present disclosure includes the following components and/or devices: a plasma separator; an adsorption chamber; and a combining chamber, each of which is described in more detail herein. The system of the present disclosure is effective to remove cytokines and other substances from the blood of a subject by assisting in carrying out the following method steps of the present disclosure: (i) passing venous blood from the subject through a plasma separator, thereby separating the blood into blood cells and plasma; (ii) passing the plasma received from the plasma separator through an adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin; (iii) combining the processed plasma, received directly from the adsorption chamber, with the blood cells in a combining chamber to form processed blood, without exchanging any of the plasma for another fluid; and (iv) transfusing the processed blood from the circuit directly into the subject, wherein no fluid besides the subject's blood is added to the circuit before the transfusing of the processed blood into the subject is completed.

In another aspect, the present disclosure is directed to a system for use in the therapeutic treatment of a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment, wherein said system comprises a plasma separator, an adsorption chamber, and a combining chamber, and wherein said system is used for said therapeutic treatment of the disease or condition by removing cytokines and other substances from blood of a subject in a closed fluid circuit, said system being effective to perform the following method steps: (i) passing venous blood from the subject through the plasma separator, thereby separating the blood into blood cells and plasma; (ii) passing the plasma received from the plasma separator through the adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin; (iii) combining the processed plasma, received directly from the adsorption chamber, with the blood cells in the combining chamber to form processed blood, without exchanging any of the plasma for another fluid; and (iv) transfusing the processed blood from the circuit directly into the subject, wherein no fluid besides the subject's blood is added to the circuit before the transfusing of the processed blood into the subject is completed.

In another aspect, the present disclosure is directed to the use of an adsorption chamber for the manufacture of a system according to the present disclosure for the therapeutic treatment of a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment.

In another aspect, the present disclosure is directed to a method of removing cytokines and other substances from blood of a subject in a closed fluid circuit. This method involves passing venous blood from the subject through a plasma separator. This step results in separating the blood into blood cells and plasma. The plasma received from the plasma separator is passed through an adsorption chamber located in the circuit to form processed plasma. The adsorption chamber is configured to include materials that adsorb cytokines in the plasma to form the processed plasma. More specifically, these adsorption materials contained in the adsorption chamber include, by weight, 50-70% activated carbon and 30-50% non-ionic resin. After passing through the adsorption chamber, the processed plasma is received directly from the adsorption chamber and combined with the subject's blood cells in a combining chamber to form processed blood. This is done without exchanging any of the plasma for another fluid. The method then involves transfusing the processed blood from the circuit directly into the subject. During the transfusing step, no fluid besides the subject's blood is added to the circuit before the transfusing of the processed blood into the subject is completed.

FIG. 1 illustrates an exemplary embodiment of a system for removing cytokines and other substances from the blood of a subject in a closed fluid circuit, as provided in the present disclosure. As shown in FIG. 1, system 1 includes plasma separator 20, adsorption chamber 30, and combining chamber 40. During operation of system 1, venous blood 12 is taken from subject 10 and passed through plasma separator 20, thereby separating venous blood 12 into blood cells 22 and plasma 24. Plasma 24 is received from plasma separator 20 and passed through adsorption chamber 30 to form processed plasma 32. Adsorption chamber 30 includes materials that adsorb cytokines and optionally other substances in plasma 24 to form processed plasma 32. As provided herein, the adsorption materials include, by weight, 50-70% activated carbon and 30-50% non-ionic resin. Processed plasma 32 is received directly from adsorption chamber 30 and combined with blood cells 22 in combining chamber 40 to form processed blood 50, without exchanging any of plasma 24 or processed plasma 32 for another fluid. Processed blood 50 is then transfused from the closed fluid circuit of system 1 directly back into subject 10. No fluid besides venous blood 12 of subject 10 is added to the closed fluid circuit of system 1 before transfusing of processed blood 50 into subject 10 is completed.

As used herein, a "closed fluid circuit" refers to an extracorporeal plasma detoxification system that is configured as a closed loop to receive venous blood from a subject and return the processed blood to the same subject, after processing the blood through a series of devices as described herein. These devices include a plasma separator, an adsorption chamber, and a combining chamber as described herein.

As used herein, a "plasma separator" refers to a device suitable for use in separating venous blood from a subject into blood cells and plasma. Suitable examples of plasma separators for use in the methods, systems, and devices of the present disclosure include, without limitation, the following: HAEMOSELECT® M 0.3 plasma filter (B. Braun Medical Inc.), HAEMOSELECT® L 0.5 plasma filter (B. Braun Medical Inc.), PLASMAFLUX® P1 dry plasma filter (Fresenius Medical Care), PLASMAFLUX® P2 dry plasma filter (Fresenius Medical Care), PLASMART™ 50 plasma filter (MEDICA S.p.A.), PLASMART™ 100 plasma filter (MEDICA S.p.A.), PLASMART™ 200 plasma filter (MEDICA S.p.A.), PLASMART™ 400 plasma filter (MEDICA S.p.A.), PLASMART™ 600 plasma filter (MEDICA S.p.A.), PLASMART™ 700 plasma filter (MEDICA S.p.A.), PLASMART™ 1000 plasma filter (MEDICA S.p.A.), PLASMAFLO™ OP-02W(L) hollow fiber plasma separator (Asahi Kasei Medical Co., Ltd.), PLASMAFLO™ OP-05W(L) hollow fiber plasma separator (Asahi Kasei Medical Co., Ltd.), PLASMAFLO™ OP-08W (L) hollow fiber plasma separator (Asahi Kasei Medical Co., Ltd.), PRISMAFLEX® TPE 1000 set plasma filter system (Baxter/Gambro), and PRISMAFLEX® TPE 2000 set plasma filter system (Baxter/Gambro).

As used herein, an "adsorption chamber" refers to a device suitable for use in removing cytokines and other substances from the blood of a subject. As described herein, the adsorption chamber of the present disclosure contains adsorption materials that adsorb cytokines in the plasma to form the processed plasma. As described in more detail herein, the adsorption chamber can also be configured to remove toxins other than cytokines from the blood of a subject.

More specifically, the adsorption chamber of the present disclosure contains adsorption materials that include, by weight, 50-70% activated carbon and 30-50% non-ionic resin, as described in more detail herein. Although the adsorption chamber must include the aforementioned activated carbon and non-ionic resin, it can also include other components, as long as they do not interfere with the functionality of the adsorption chamber as described herein.

As used herein, the term "adsorption materials" refers to the materials contained in the adsorption chamber that are effective to remove cytokines and other substances of interest from the blood of a subject. In certain instances, the term "materials" may be used to denote "adsorption materials" of the present disclosure. More specifically, the adsorption materials of the present disclosure include activated carbon and non-ionic resins. When used in the adsorption chamber of the present disclosure, the adsorption materials are present in an amount, by weight, of 50-70% activated carbon and 30-50% non-ionic resin. In one embodiment, the activated carbon includes at least one activated carbon material selected from, for example, uncoated coconut shell granule charcoal, uncoated organic granule charcoal, uncoated synthetic carbon, and the like. Suitable non-ionic resins can include, without limitation, at least one resin material selected from a non-ionic aliphatic ester resin, a non-ionic polystyrene divinyl benzene resin, an agarose media with hydrophobic interactive chromatography, and other non-biologic adsorptive resins. A suitable non-ionic aliphatic ester resin can include, without limitation, AMBERLITE® XAD-7HP. A suitable non-ionic polystyrene divinyl benzene resin can include, without limitation, AMBERCHROM® GC300C.

The non-ionic resins suitable for use in the methods, systems, and devices of the present disclosure are further described below.

In certain embodiments of the methods, systems, and devices of the present disclosure, non-ionic exchange resins are exclusively used in accordance with the teachings of the present disclosure because they will not bind (and thus removed from the blood) essential cations and anions such as, but not limited to, calcium, magnesium, sodium, potassium, chloride, carbonates, and other ionic species. This is important when recirculating patient's plasma through an adsorptive device since changes in electrolytes results in changes in osmolality of a patient's blood chemistry which is not desired.

Specific non-limiting examples of non-ionic exchange resins suitable for use with the methods, systems, and devices of the present disclosure can include, without limitation, AMBERLITE™ XAD-7 HP, AMBERCHROM™ CG300-C, and hydrophobic interaction chromatography resins (Butyl-S Sepharose 6, Butyl Sepharose 4, Capto Pheno, Capto Butyl, Capto Octyl, Capto Phenyl ImRes, Capto Butyl ImpRes, Phenyl Sepharose High Performance, Butyl Sepharose High Performance, Phenyl Sepharose 6 FastFlow low-sub, Phenyl Sepharose 6 FastFlow high-sub).

AMBERLITE™ is a group of polymeric synthetic resins made by the Rohm and Haas Company having a North American headquarters at 100 Independence Mall West Philadelphia, PA. 19106-2399. AMBERLITE™ resins are available worldwide through a distributor network know to those skilled in the art. In one specific embodiment, the present disclosure involves the use of AMBERLITE™ XAD-7 HP, which is an aliphatic ester resin having an average surface area of approximately 500 $m^2/g$ and an average pore size of approximately 450 Angstroms and a mean diameter of approximately 560 microns.

AMBERCHROME™ CG300-G is a synthetic non-ionic exchange resin, also manufactured by Rohm and Haas, made from polystyrene divinyl benzene having an average surface area of approximately 700 $m^2/g$ with an average pore size of 300 Angstroms; mean particle diameter ranges from approximately 35 microns to approximately 120 microns.

As used herein, hydrophobic interaction chromatography resins have particle diameters between 30 and 200 microns and are media produced by GE Healthcare Bio Sciences AB, Bjorkgaten 30, 751 84 Uppsala Sweden.

In one embodiment, the adsorption chamber is constructed from a polymer including, without limitation, polycarbonate, polypropylene, a Lexan co-polymer, polytetrafluoroethylene, and other medical grade polymers suitable for injection or blow molding.

In another embodiment, the adsorption chamber and/or the materials contained in the adsorption chamber are coated with human serum albumin and an anticoagulant added to physiological saline as a solution prior to clinical use.

Suitable anticoagulants for use in the methods, systems, and devices of the present disclosure include, without limitation, sodium heparin and citrate dextrose solution ACD-A.

Figure 2:
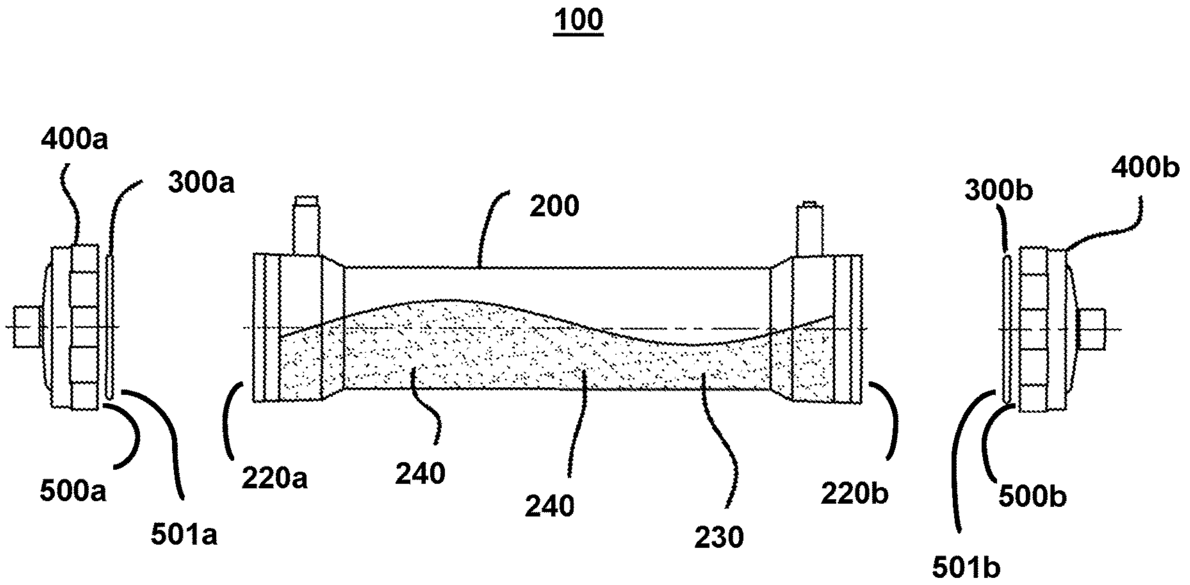
FIG. 2 is a schematic of an exemplary embodiment of an adsorption chamber for use in the methods, systems, and devices for removing cytokines and other substances from blood of a subject in a closed fluid circuit, as provided in the present disclosure.

FIG. 2 illustrates an exemplary embodiment of an adsorption chamber for use in the methods, systems, and devices of the present disclosure. As shown in FIG. 2, adsorption chamber 100 includes housing 200, porous membranes 300*a*, 300*b*, and endcaps 400*a*, 400*b*. Housing 200 includes hollow tube 210 with opposing open ends 220*a*, 220*b*. Housing 200 contains activated carbon 230 and one or more non-ionic resin 240. Porous membrane filters 300*a*, 300*b* covers each of ends 220*a*, 220*b* of housing 200, each porous membrane filter 300*a*, 300*b* creating a barrier for maintaining activated carbon 230 and non-ionic resins 240 within housing 200 while allowing for passage therethrough of plasma during performance of the method of the present disclosure. Endcaps 400*a*, 400*b* fitted to each of ends 220*a*, 220*b* of housing 200, where each endcap 400*a*, 400*b* is configured to keep its corresponding porous membrane filter 300*a*, 300*b* in place and to maintain a seal between each endcap 400*a*, 400*b* and the corresponding end 220*a*, 220*b* of housing 200.

In certain embodiments of the adsorption chamber of the present disclosure, each endcap includes a groove molded into its entire inner circumference. As provided herein, the groove is configured to facilitate mating of each endcap with the corresponding end of the housing.

In certain embodiments, the groove is configured to receive a quantity of adhesive. As shown in the exemplary embodiment adsorption chamber 100 of FIG. 2, adhesive 500*a*, 500*b* is deposited in the groove so as to aid in adhering porous membrane filters 300*a*, 300*b* to endcap 400*a*, 400*b*. In certain embodiments, another quantity of adhesive 501*a*, 501*b* is deposited between each endcap 400*a*, 400*b* and its corresponding porous membrane filter 300*a*, 300*b* to provide further adhesion between endcap 400*a*, 400*b* and the corresponding end 220*a*, 220*b* of the housing 200.

In certain embodiments, the ends of the housing are threaded and the corresponding endcaps are also threaded so as to mate with one another.

In certain embodiments, the housing is in the form of a tube comprising at least one of polypropylene, polytetrafluoroethylene, or other medical grade tubing materials.

In another aspect, the present disclosure is directed to a method for therapeutic treatment of a subject involving the use of the methods, systems, and devices of the present disclosure for removing cytokines and other substances from the blood of the subject, thereby providing therapeutic treatment to the subject. In one embodiment, the therapeutic treatment of the present disclosure can be administered via use of a standard venous access in an outpatient treatment setting.

In accordance with the method for therapeutic treatment of the present disclosure, the therapeutic treatment can be for a disease or condition that can include, without limitation, sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment.

As provided herein, the autoimmune disease can include, without limitation, inflammatory arthritis, psoriasis, Crohn's disease, ulcerative colitis, inflammatory bowel disease, uveitis, and the like.

As provided herein, the inflammation can be treated, without limitation, using an age defying anti-inflammation application such as cosmetic, pain, and discomfort applications.

In a specific embodiment, the present disclosure provides an extracorporeal plasma detoxification system that can remove toxins associated with and resulting from sepsis, liver failure, renal failure, acute respiratory distress, auto immune, viral, poison, tick, pancreatic cancer bilirubin management, post-surgery inflammation management and other inflammation disease from the plasma of patients in need of therapeutic treatment. One embodiment of a system of the present disclosure can include, without limitation, an extracorporeal system that can generally be used to remove blood via a catheter, AV fistula or graft from a patient in need of plasma detoxification. Blood is removed from a large vein of a patient via one lumen of a conventional dual lumen catheter connected to a centrifugal apheresis pump where the blood cells are separated from the plasma fraction of the blood. The separated blood leaves the centrifugal apheresis pump and can continue in one of two pathways. Blood cells are returned to the patient while the separated plasma enters and passes through the adsorption column which is the toxin removal device of the present disclosure, which contains a mixture of adsorbent materials. The adsorptive toxin removal device removes both protein-bound and soluble toxins. After leaving the adsorbent column, the plasma flow is recombined with the patient's blood cells.

EXEMPLARY EMBODIMENTS

The following embodiments are exemplary and are not intended to limit the present invention.

Embodiment 1

A system for removing cytokines and other substances from blood of a subject in a closed fluid circuit, said system comprising components effective to perform the following method steps:

(a) passing venous blood from the subject through a plasma separator, thereby separating the blood into blood cells and plasma;

(b) passing the plasma received from the plasma separator through an adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin;

(c) combining the processed plasma, received directly from the adsorption chamber, with the blood cells in a combining chamber to form processed blood, without exchanging any of the plasma for another fluid; and (d) transfusing the processed blood from the circuit directly into the subject, wherein no fluid besides the subject's blood is added to the circuit before the transfusing of the processed blood into the subject is completed.

Embodiment 2

The system according to Embodiment 1, wherein the non-ionic resin comprises at least one resin material selected from the group consisting of a non-ionic aliphatic ester resin, a non-ionic polystyrene divinyl benzene resin, an agarose media with hydrophobic interactive chromatography, and other non-biologic adsorptive resins.

Embodiment 3

The system according to Embodiment 2, wherein the non-ionic aliphatic ester resin is AMBERLITE® XAD-7HP.

Embodiment 4

The system according to Embodiment 2, wherein the non-ionic polystyrene divinyl benzene resin is AMBERCHROM® GC300C.

Embodiment 5

The system according to Embodiment 2, wherein the activated carbon comprises at least one activated carbon material selected from the group consisting of uncoated coconut shell granule charcoal, uncoated organic granule charcoal, and uncoated synthetic carbon.

Embodiment 6

The system according to Embodiment 1, wherein the adsorption chamber is constructed from a polymer selected from the group consisting of polycarbonate, polypropylene, a Lexan co-polymer, polytetrafluoroethylene, and other medical grade polymers suitable for injection or blow molding.

Embodiment 7

The system according to Embodiment 1, wherein the adsorption chamber comprises:

(a) a housing comprising a hollow tube with opposing open ends, said housing containing the activated carbon and non-ionic resin;
(b) porous membrane filters covering each of the ends of the housing, each porous membrane filter creating a barrier for maintaining the activated carbon and non-ionic resin within the housing while allowing for passage therethrough of the plasma during performance of the method steps; and
(c) endcaps fitted to each of the ends of the housing, wherein each endcap is configured to keep its corresponding porous membrane filter in place and to maintain a seal between the endcap and the corresponding end of the housing.

Embodiment 8

The system according to Embodiment 7, wherein each endcap includes a groove molded into its entire inner circumference, said groove being configured to facilitate mating of each endcap with the corresponding end of the housing.

Embodiment 9

The system according to Embodiment 8, wherein said groove is configured to receive a quantity of adhesive, and said adhesive being deposited in the groove so as to aid in adhering the porous membrane filter to the endcap.

Embodiment 10

The system according to Embodiment 9, wherein another quantity of adhesive is deposited between each endcap and its corresponding porous membrane filter to provide further adhesion between the endcap and the corresponding end of the housing.

Embodiment 11

The system according to Embodiment 7, wherein the ends of the housing are threaded and the corresponding endcaps are also threaded so as to mate with one another.

Embodiment 12

The system according to Embodiment 7, wherein the housing is in the form of a tube comprising at least one of polypropylene, polytetrafluoroethylene, or other medical grade tubing materials.

Embodiment 13

The system according to Embodiment 1, wherein the adsorption chamber and/or the materials in the adsorption chamber are coated with human serum albumin and an anticoagulant added to physiological saline as a delivery solution prior to clinical use.

Embodiment 14

The system according to Embodiment 13, wherein the anticoagulant is selected from the group consisting of sodium heparin and citrate dextrose solution ACD-A.

Embodiment 15

The system according to Embodiment 1, wherein said adsorption chamber is effective to remove toxins other than cytokines from blood of the subject.

Embodiment 16

A system for use in the therapeutic treatment of a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment, wherein said system comprises a plasma separator, an adsorption chamber, and a combining chamber, and wherein said system is used for said therapeutic treatment of the disease or condition by removing cytokines and other substances from blood of a subject in a closed fluid circuit, said system being effective to perform the following method steps:

(i) passing venous blood from the subject through the plasma separator, thereby separating the blood into blood cells and plasma;
(ii) passing the plasma received from the plasma separator through the adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin;

(iii) combining the processed plasma, received directly from the adsorption chamber, with the blood cells in the combining chamber to form processed blood, without exchanging any of the plasma for another fluid; and (iv) transfusing the processed blood from the circuit directly into the subject, wherein no fluid besides the subject's blood is added to the circuit before the transfusing of the processed blood into the subject is completed.

Embodiment 17

The system according to Embodiment 16, wherein said autoimmune disease is selected from the group consisting of inflammatory arthritis, psoriasis, Crohn's disease, ulcerative colitis, inflammatory bowel disease, and uveitis.

Embodiment 18

The system according to Embodiment 16, wherein the non-ionic resin comprises at least one resin material selected from the group consisting of a non-ionic aliphatic ester resin, a non-ionic polystyrene divinyl benzene resin, an agarose media with hydrophobic interactive chromatography, and other non-biologic adsorptive resins.

Embodiment 19

The system according to Embodiment 18, wherein the non-ionic aliphatic ester resin is AMBERLITE® XAD-7HP.

Embodiment 20

The system according to Embodiment 18, wherein the non-ionic polystyrene divinyl benzene resin is AMBERCHROM® GC300C.

Embodiment 21

The system according to Embodiment 18, wherein the activated carbon comprises at least one activated carbon material selected from the group consisting of uncoated coconut shell granule charcoal, uncoated organic granule charcoal, and uncoated synthetic carbon.

Embodiment 22

The system according to Embodiment 16, wherein the adsorption chamber is constructed from a polymer selected from the group consisting of polycarbonate, polypropylene, a Lexan co-polymer, polytetrafluoroethylene, and other medical grade polymers suitable for injection or blow molding.

Embodiment 23

The system according to Embodiment 16, wherein the adsorption chamber comprises:

(a) a housing comprising a hollow tube with opposing open ends, said housing containing the activated carbon and non-ionic resin;

(b) porous membrane filters covering each of the ends of the housing, each porous membrane filter creating a barrier for maintaining the activated carbon and non-ionic resin within the housing while allowing for passage therethrough of the plasma during performance of the method steps; and (c) endcaps fitted to each of the ends of the housing, wherein each endcap is configured to keep its corresponding porous membrane filter in place and to maintain a seal between the endcap and the corresponding end of the housing.

Embodiment 24

The system according to Embodiment 23, wherein each endcap includes a groove molded into its entire inner circumference, said groove being configured to facilitate mating of each endcap with the corresponding end of the housing.

Embodiment 25

The system according to Embodiment 24, wherein said groove is configured to receive a quantity of adhesive, and said adhesive being deposited in the groove so as to aid in adhering the porous membrane filter to the endcap.

Embodiment 26

The system according to Embodiment 25, wherein another quantity of adhesive is deposited between each endcap and its corresponding porous membrane filter to provide further adhesion between the endcap and the corresponding end of the housing.

Embodiment 27

The system according to Embodiment 23, wherein the ends of the housing are threaded and the corresponding endcaps are also threaded so as to mate with one another.

Embodiment 28

The system according to Embodiment 23, wherein the housing is in the form of a tube comprising at least one of polypropylene, polytetrafluoroethylene, or other medical grade tubing materials.

Embodiment 29

The system according to Embodiment 16, wherein the adsorption chamber and/or the materials in the adsorption chamber are coated with human serum albumin and an anticoagulant added to physiological saline as a delivery solution prior to clinical use.

Embodiment 30

The system according to Embodiment 29, wherein the anticoagulant is selected from the group consisting of sodium heparin and citrate dextrose solution ACD-A.

Embodiment 31

The system according to Embodiment 16, wherein said adsorption chamber is effective to remove toxins other than cytokines from blood of the subject.

Embodiment 32

Use of an adsorption chamber for the manufacture of a system according to any one of Embodiments 16-31 for the therapeutic treatment of a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment.

Embodiment 33

The use according to Embodiment 32, wherein said autoimmune disease is selected from the group consisting of inflammatory arthritis, psoriasis, Crohn's disease, ulcerative colitis, inflammatory bowel disease, and uveitis.

Embodiment 34

A method of removing cytokines and other substances from blood of a subject in a closed fluid circuit, said method comprising:

(a) passing venous blood from the subject through a plasma separator, thereby separating the blood into blood cells and plasma;

(b) passing the plasma received from the plasma separator through an adsorption chamber located in the circuit to form processed plasma, wherein materials in the adsorption chamber adsorb cytokines in the plasma to form the processed plasma, said materials comprising, by weight, 50-70% activated carbon and 30-50% non-ionic resin;

(c) combining the processed plasma, received directly from the adsorption chamber, with the blood cells in a combining chamber to form processed blood, without exchanging any of the plasma for another fluid; and (d) transfusing the processed blood from the circuit directly into the subject, wherein no fluid besides the subject's blood is added to the circuit before the transfusing of the processed blood into the subject is completed.

Embodiment 35

The method according to Embodiment 34, wherein the non-ionic resin comprises at least one resin material selected from the group consisting of a non-ionic aliphatic ester resin, a non-ionic polystyrene divinyl benzene resin, an agarose media with hydrophobic interactive chromatography, and other non-biologic adsorptive resins.

Embodiment 36

The method according to Embodiment 35, wherein the non-ionic aliphatic ester resin is AMBERLITE® XAD-7HP.

Embodiment 37

The method according to Embodiment 35, wherein the non-ionic polystyrene divinyl benzene resin is AMBERCHROM® GC300C.

Embodiment 38

The method according to Embodiment 35, wherein the activated carbon comprises at least one activated carbon material selected from the group consisting of uncoated coconut shell granule charcoal, uncoated organic granule charcoal, and uncoated synthetic carbon.

Embodiment 39

The method according to Embodiment 34, wherein the adsorption chamber is constructed from a polymer selected from the group consisting of polycarbonate, polypropylene, a Lexan co-polymer, polytetrafluoroethylene, and other medical grade polymers suitable for injection or blow molding.

Embodiment 40

The method according to Embodiment 34, wherein the adsorption chamber comprises:

(a) a housing comprising a hollow tube with opposing open ends, said housing containing the activated carbon and non-ionic resin;

(b) porous membrane filters covering each of the ends of the housing, each porous membrane filter creating a barrier for maintaining the activated carbon and non-ionic resin within the housing while allowing for passage therethrough of the plasma during performance of the method; and (c) endcaps fitted to each of the ends of the housing, wherein each endcap is configured to keep its corresponding porous membrane filter in place and to maintain a seal between the endcap and the corresponding end of the housing.

Embodiment 41

The method according to Embodiment 40, wherein each endcap includes a groove molded into its entire inner circumference, said groove being configured to facilitate mating of each endcap with the corresponding end of the housing.

Embodiment 42

The method according to Embodiment 41, wherein said groove is configured to receive a quantity of adhesive, and said adhesive being deposited in the groove so as to aid in adhering the porous membrane filter to the endcap.

Embodiment 43

The method according to Embodiment 42, wherein another quantity of adhesive is deposited between each endcap and its corresponding porous membrane filter to provide further adhesion between the endcap and the corresponding end of the housing.

Embodiment 44

The method according to Embodiment 41, wherein the ends of the housing are threaded and the corresponding endcaps are also threaded so as to mate with one another.

Embodiment 45

The method according to Embodiment 40, wherein the housing is in the form of a tube comprising at least one of polypropylene, polytetrafluoroethylene, or other medical grade tubing materials.

Embodiment 46

The method according to Embodiment 34, wherein the adsorption chamber and/or the materials in the adsorption chamber are coated with human serum albumin and an anticoagulant added to physiological saline as a solution prior to clinical use.

Embodiment 47

The method according to Embodiment 46, wherein the anticoagulant is selected from the group consisting of sodium heparin and citrate dextrose solution ACD-A.

Embodiment 48

The method according to Embodiment 34, wherein said adsorption chamber is effective to remove toxins other than cytokines from blood of the subject.

Embodiment 49

A method for therapeutic treatment of a subject, said method comprising: performing the method according to any one of Embodiments 34-47 to remove cytokines and other substances from the blood of the subject, thereby providing therapeutic treatment to the subject.

Embodiment 50

The method according to Embodiment 49, wherein the therapeutic treatment is for a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment.

Embodiment 51

The method according to Embodiment 50, wherein said autoimmune disease is selected from the group consisting of inflammatory arthritis, psoriasis, Crohn's disease, ulcerative colitis, inflammatory bowel disease, and uveitis.

Embodiment 52

The method according to Embodiment 50, wherein said inflammation is treated using an age defying anti-inflammation application selected from the group consisting of cosmetic, pain, and discomfort applications.

Embodiment 53

The method according to Embodiment 49, wherein said therapeutic treatment is administered via use of a standard venous access in an outpatient treatment setting.

Embodiment 54

The method according to Embodiment 49 further comprising introducing an anticoagulant into the circuit.

Embodiment 55

The method according to Embodiment 54, wherein the anticoagulant is a citrate dextrose solution ACD-D.

Embodiment 56

The method according to Embodiment 49 further comprising removing toxins from the blood of the subject with the adsorption chamber.

Numeric ranges are inclusive of the numbers defining the range. The term about is used herein to mean plus or minus up to ten percent (10%) of a value. For example, "about 100" refers to any number between 90 and 110.

The headings provided herein are not limitations of the various aspects or embodiments of the invention, which can be had by reference to the specification as a whole. Accordingly, the terms defined immediately below are more fully defined by reference to the specification as a whole.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the methods, systems, and devices disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Other advantages which are obvious and which are inherent to the disclosure will be evident to one skilled in the art. It will be understood that certain features and sub-combinations are of utility and may be employed without reference to other features and sub-combinations. This is contemplated by and is within the scope of the claims. Since many possible embodiments may be made of the disclosure without departing from the scope thereof, it is to be understood that all matter herein set forth or shown in the accompanying drawings is to be interpreted as illustrative and not in a limiting sense.

What is claimed is:

1. A method of removing cytokines and other substances from blood of a subject in a closed fluid circuit, said method comprising:

providing a system comprising a plasma separator, an adsorption chamber located in the circuit, a combining chamber, and a catheter, wherein the plasma separator comprises a centrifugal apheresis pump, wherein the adsorption chamber comprises materials comprising, by weight, 50-70% activated carbon and 30-50% non-ionic resin, and wherein, prior to passage of blood through the adsorption chamber in safe clinical use, the materials are not coated with human albumin, wherein the catheter is connected to the centrifugal apheresis pump;

passing venous blood of the subject from the catheter through the centrifugal apheresis pump of the plasma separator of the system, thereby separating the blood into blood cells and plasma;

passing the plasma directly received from the plasma separator directly through the adsorption chamber located in the circuit of the system to form processed plasma, wherein, prior to the passing of the plasma, the adsorption chamber is not coated with albumin;

combining the processed plasma, received directly from the adsorption chamber, with the blood cells in the combining chamber to form processed blood, without exchanging any of the plasma for another fluid; and transfusing the processed blood from the circuit directly into the subject, wherein no fluid besides the subject's blood is added to the circuit before the transfusing of the processed blood into the subject is completed.

2. The method according to claim 1, wherein the non-ionic resin comprises at least one resin material selected from the group consisting of a non-ionic aliphatic ester resin, a non-ionic polystyrene divinyl benzene resin, an agarose media with hydrophobic interactive chromatography, and other non-biologic adsorptive resins.

3. The method according to claim 2, wherein the non-ionic aliphatic ester resin is a non-ionic, aliphatic acrylic resin having an average surface area of approximately 500 $m^2/g$ and an average pore size of approximately 450 Angstroms and a mean diameter of approximately 560 microns.

4. The method according to claim 2, wherein the non-ionic polystyrene divinyl benzene resin is a synthetic non-ionic exchange resin made from polystyrene divinyl benzene having an average surface area of approximately 700 $m^2/g$ with an average pore size of 300 Angstroms and a mean particle diameter ranging from approximately 35 microns to approximately 120 microns.

5. The method according to claim 2, wherein the activated carbon comprises at least one activated carbon material selected from the group consisting of uncoated coconut shell granule charcoal, uncoated organic granule charcoal, and uncoated synthetic carbon.

6. The method according to claim 1, wherein the adsorption chamber is constructed from a polymer selected from the group consisting of polycarbonate, polypropylene, a Lexan co-polymer, polytetrafluoroethylene, and other medical grade polymers suitable for injection or blow molding.

7. The method according to claim 1, wherein the adsorption chamber comprises:

a housing comprising a hollow tube with opposing open ends, said housing containing the activated carbon and non-ionic resin;

porous membrane filters covering each of the ends of the housing, each porous membrane filter creating a barrier for maintaining the activated carbon and non-ionic resin within the housing while allowing for passage therethrough of the plasma during performance of the method; and endcaps fitted to each of the ends of the housing, wherein each endcap is configured to keep its corresponding porous membrane filter in place and to maintain a seal between the endcap and the corresponding end of the housing.

8. The method according to claim 7, wherein each endcap includes a groove molded into its entire inner circumference, said groove being configured to facilitate mating of each endcap with the corresponding end of the housing.

9. The method according to claim 8, wherein said groove is configured to receive a quantity of adhesive, and said adhesive being deposited in the groove so as to aid in adhering the porous membrane filter to the endcap.

10. The method according to claim 9, wherein another quantity of adhesive is deposited between each endcap and its corresponding porous membrane filter to provide further adhesion between the endcap and the corresponding end of the housing.

11. The method according to claim 8, wherein the ends of the housing are threaded and the corresponding endcaps are also threaded so as to mate with one another.

12. The method according to claim 7, wherein the housing is in the form of a tube comprising at least one of polypropylene, polytetrafluoroethylene, or other medical grade tubing materials.

13. The method according to claim 1, wherein the adsorption chamber and/or the materials in the adsorption chamber are coated with an anticoagulant added to physiological saline as a solution prior to clinical use.

14. The method according to claim 13, wherein the anticoagulant is selected from the group consisting of sodium heparin and citrate dextrose solution ACD-A.

15. The method according to claim 1, wherein said adsorption chamber is effective to remove toxins other than cytokines from blood of the subject.

16. A method for therapeutic treatment of a subject, said method comprising:

performing the method according to claim 1 to remove cytokines and other substances from the blood of the subject, thereby providing therapeutic treatment to the subject.

17. The method according to claim 16, wherein the therapeutic treatment is for a disease or condition selected from the group consisting of sepsis, liver failure, viral infection, acute respiratory distress, renal failure, inflammation, poisoning, drug overdose, autoimmune disease, tick-borne illness, chemical or nerve agent exposure, burn biliary obstruction, post-surgery inflammation, bacterial infection, complications caused by smoke inhalation, complications as a result of any form of injury or trauma, and complications as a result of any form of cancer or cancer treatment.

18. The method according to claim 16 further comprising introducing an anticoagulant into the circuit.

19. The method according to claim 16 further comprising removing toxins from the blood of the subject with the adsorption chamber.

* * * * *